United States Patent [19]

Neumann

[11] Patent Number: 4,567,271
[45] Date of Patent: Jan. 28, 1986

[54] BENZOXADIAZOLES AND BENZOTHIADIAZOLES

[75] Inventor: Peter Neumann, Berne, Switzerland

[73] Assignee: Sandoz Ltd., Basle, Switzerland

[21] Appl. No.: 614,650

[22] Filed: May 29, 1984

Related U.S. Application Data

[60] Division of Ser. No. 359,751, Mar. 19, 1982, Pat. No. 4,466,972, which is a continuation of Ser. No. 173,305, Jul. 29, 1980, abandoned, which is a continuation-in-part of Ser. No. 101,591, Dec. 10, 1979, abandoned, which is a continuation-in-part of Ser. No. 915,858, Jun. 15, 1978, abandoned.

[30] Foreign Application Priority Data

Jun. 20, 1977 [CH] Switzerland ............... 7520/77

[51] Int. Cl.⁴ ................ A61K 31/44; C07D 513/00
[52] U.S. Cl. ................................. 546/271
[58] Field of Search ............ 544/80; 546/271

[56] References Cited

U.S. PATENT DOCUMENTS 4,466,972 8/1984 Neumann ............... 424/266

Primary Examiner—Christopher A. Henderson
Attorney, Agent, or Firm—Gerald D. Sharkin; Robert S. Honor; Joseph J. Borovian

[57] ABSTRACT

Compounds of formula I,

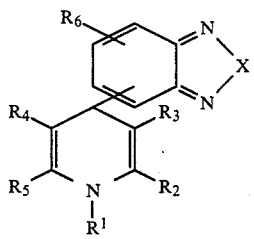

wherein X is oxygen or sulphur, and $R_1$–$R_6$ are various substituents. The compounds are useful for treating coronary insufficiency, intermittent claudication, cerebrovascular insults, spasms in muscles and hypertension.

4 Claims, No Drawings

BENZOXADIAZOLES AND BENZOTHIADIAZOLES

This is a division of application Ser. No. 359,751, filed Mar. 19, 1982, now issued as U.S. Pat. No. 4,466,972, which in turn is a continuation of application Ser. No. 173,305, filed July 29, 1980, now abandoned, which is turn is a continuation-in-part of Ser. No. 101,591, filed Dec. 10, 1979, now abandoned, which in turn is a continuation-in-part of Ser. No. 915,585, filed June 15, 1978, now abandoned.

The present invention relates to benzoxadiazoles and benzothiadiazoles having a 4-dihydropyridine moiety.

The present invention provides in particular compounds of formula I,

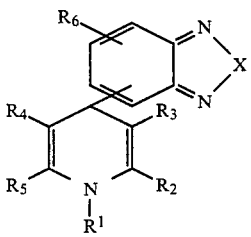

wherein
$R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently are CN, $COR_7$, $COOR_7$, $S(O)_n R_7$ or

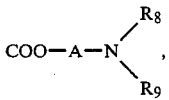

wherein
n is 0, 1 or 2,
$R_7$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), di[alkyl($C_{1-4}$)]aminoalkyl, phenyl, phenylalkyl($C_{7-10}$), a 5- or 6-membered heterocyclic ring containing one heteroatom selected from nitrogen, oxygen or sulphur and may contain additionally 1, 2 or 3 ring nitrogen atoms, or alkyl($C_{1-4}$) substituted by a 5- or 6-membered heterocyclic ring containing one heteroatom selected from nitrogen, oxygen or sulphur and may contain additionally 1, 2 or 3 ring nitrogen atoms,
A is alkylene($C_{1-6}$),
$R_8$ and $R_9$, independently, are alkyl($C_{1-6}$), alkenyl or alkinyl($C_{3-6}$), cycloalkyl($C_{3-7}$), cycloalkylalkyl($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), di[alkyl($C_{1-4}$)]aminoalkyl, phenyl, phenylalkyl($C_{7-10}$), or
$R_8$ and $R_9$ together with the nitrogen atom form a 5-, 6- or 7-membered heterocyclic ring, which may contain a further heteromember selected from oxygen, sulphur and a group $=N-R_{10}$, wherein $R_{10}$ is alkyl ($C_{1-4}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro, hydroxy, azido, amino, alkyl($C_{1-4}$)amino, di[alkyl($C_{1-4}$)]amino, alkanoyl($C_{1-5}$)amino, carbalkoxy($C_{2-5}$), aminocarbonyl, trifluoromethoxy, cyano, sulfamyl, alkyl($C_{1-4}$)sulfamyl or di[alkyl($C_{1-4}$)]sulfamyl, and X is oxygen or sulphur.

One group of compounds comprises compounds of formula I as defined above, with the proviso that, when $R_1$ is hydrogen, alkyl($C_{1-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenylring being unsubstituted or mono-, di- or tri-substituted independently by halogen, hydroxy, alkyl($C_{1-4}$) or alkoxy($C_{1-4}$), $R_2$ and $R_5$, independently, are hydrogen or alkyl($C_{1-6}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro or hydroxy, and X is oxygen or sulphur, then at least one of the substituents $R_3$ and $R_4$ is other than $COR_7{}^I$, wherein $R_7{}^I$ is alkyl($C_{1-6}$), alkenyl($C_{3-6}$), alkinyl($C_{3-6}$), cycloalkyl($C_{3-7}$), cycloalkylalkyl($C_{4-8}$), and is other than $COOR_7{}^{II}$, wherein $R_7{}^{II}$ is alkyl($C_{1-6}$), alkenyl ($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$) or hydroxyalkoxyalkyl($C_{4-8}$).

In any of the above radicals alkyl of 1 to 6 carbon atoms is preferably of 1 to 4 carbon atoms, especially of 1 to 2 carbon atoms. Any alkyl, alkoxy, alkylthio or alkylsulfonyl radical of 1 to 4 carbon atoms is preferably of 1 to 2 carbon atoms. The hydroxy, alkoxy, hydroxyalkoxy, amino or alkylamino group of the hydroxyalkyl, alkoxyalkyl, hydroxyalkoxyalkyl, aminoalkyl or alkylaminoalkyl moiety in $COOR_7$ is preferably not attached to the $\alpha$-carbon atom and is preferably attached to the distal terminal carbon atom. Any hydroxyalkyl, alkoxyalkyl, hydroxyalkoxyalkyl, aminoalkyl or alkylaminoalkyl radical preferably has an ethylene or propylene moiety substituted by hydroxy, alkoxy, hydroxyalkoxy, amino or alkylamino respectively. The alkyl moiety of cycloalkylalkyl is conveniently methyl. Halogen means fluorine, chlorine or bromine and is especially chlorine. Cycloalkyl or the cycloalkyl moiety of cycloalkylalkyl is conveniently cyclopropyl or cyclopentyl or cyclohexyl. The multiple bond of alkenyl, alkinyl or phenylalkenyl in $R_1$ or $COOR_7$ is preferably not in the $\alpha,\beta$ position. Alkenyl or alkinyl preferably has 3 to 5 carbon atoms. Alkenyl is conveniently allyl or 2-methylallyl. Alkinyl is conveniently propinyl. Phenylalkenyl preferably has the trans-configuration and is for example cinnamyl. When $R_1$ is optionally substituted phenylalkyl, the phenyl group is preferably unsubstituted. When the phenyl group is di- or tri-substituted, preferably the substituents are the same.

When $R_7$ is alkyl, this is preferably branched. When $R_7$ contains a heterocyclic ring this may be for example furyl, thienyl, pyrrolyl, thiazolyl, isothiazolyl, thiadiazolyl, oxazolyl, isoxazolyl, oxadiazolyl, imidazolyl, pyrazolyl, triazolyl, tetrazolyl, pyridyl, pyrimidinyl, pyrazinyl, pyridazinyl, piperidinyl, morpholinyl or triazinyl.

When $R_8$ and $R_9$ together with the nitrogen atom to which they are bound, form a heterocyclic ring, this is preferably saturated and may be for example pyrrolidine, piperidine, piperazine, N-alkylpiperazine, morpholine, azepane, diazepane or N-alkyl-diazepane.

$R_1$ is conveniently hydrogen. $R_2$ is conveniently identical to $R_5$. $R_2$ is conveniently alkyl. $R_3$ and/or $R_4$ is conveniently $COOR_7$ or

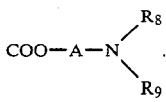

$R_7$ is conveniently alkyl, preferably branched or alkoxyalkyl, where the alkoxy moiety is preferably branched. A is conveniently ethylene. $R_8$ and $R_9$ are conveniently alkyl or phenylalkyl.

The present invention also provides a process for the production of a compound of formula I as defined above, comprising replacing the moiety —HC=Y in a compound of formula II,

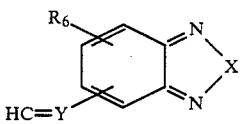

wherein
$R_6$ and X are as defined above, and —HC=Y is
(i) formyl,
(ii) a radical of formula

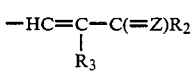

or
(iii) a radical of formula

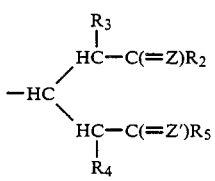

wherein
Z and Z' are independently oxygen or $NR_1$, and $R_1$ to $R_5$ are as defined above,
by a moiety of formula III,

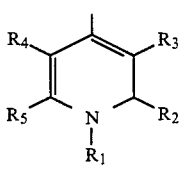

wherein $R_1$ to $R_5$ are as defined above.

The process may be effected in conventional manner for analogous dihydropyridine syntheses, e.g. according to Hantzsch. When the moiety —HC=Y is formyl and when it is desired to produce a compound of formula I, wherein $R_2$ is identical to $R_5$ and $R_3$ is identical to $R_4$, it is convenient to react a compound of formula II with a compound of formula IV,

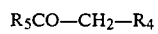

wherein $R_4$ and $R_5$ are as defined above, in the presence of a compound of formula V,

wherein $R_1$ is as defined above.

Preferably at least 2 moles of a compound of formula IV per mole of a compound of formula II are present. Alternatively a compound of formula II may be reacted with a compound of formula VI,

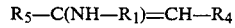

wherein $R_1$, $R_4$ and $R_5$ are as defined above.

Preferably at least 2 moles of a compound of formula VI per mole of a compound of formula II are present. Preferably also $R_1$ is hydrogen.

When the moiety —HC=Y is formyl and preferably when it is desired to produce a compound of formula I wherein $R_2$ is different to $R_5$ and/or $R_3$ is different to $R_4$, it is also possible to react such a compound of formula II with a compound of formula IV and a compound of formula VII, $$R_2—C(NH—R_1)=CH—R_3 \quad VII$$

wherein $R_2$, $R_1$ and $R_3$ are as defined above.

It will be appreciated that a compound of formula VI may be formed as an intermediate during the reaction of a compound of formula IV and a compound of formula V. A compound of formula II, wherein —HC=Y is a radical ii) or iii), may be formed as an intermediate in the above reactions. They may however be produced by different processes.

Alternatively or particularly for the production of a compound of formula I, wherein $R_2$ is different to $R_5$ and/or $R_3$ is different to $R_4$, it is convenient to react a compound of formula II, wherein the moiety —HC=Y is a radical ii) with a compound of formula IV or VI, and where appropriate, with a compound of formula V. A compound of formula II, wherein the moiety —HC=Y is a radical iii) may be an intermediate.

In the above reactions it is possible in certain instances when $R_2$, $R_3$, $R_4$ and $R_5$ are not identical that more than one isomer of formula I may be formed. If so these may be separated in conventional manner, e.g. by column or thin layer chromatography.

When the starting material is a compound of formula II, wherein —HC=Y is a radical iii), the reaction is a ring cyclisation. When Z and Z' are both oxygen, then an amine of formula V should be present.

However, all the above reactions may be effected under the same conditions.

The reaction may be effected conveniently in solution. A suitable solvent is water, ethanol, dioxane, dimethyl formamide, dimethyl sulphoxide, pyridine or glacial acetic acid. Suitable reaction temperatures may be from 20° to 160° C., preferably from 60° to 120° C.

Insofar as the production of starting materials is not particularly described these compounds are known or may be produced in analogous manner to known compounds.

The basic compounds of formula I may be converted into acid addition salt forms in conventional manner and vice versa. Suitable acids are e.g. maleic acid, oxalic acid, methanesulphonic acid, hydrochloric acid and hydrobromic acid.

The present invention provides a group of compounds of formula Ia,

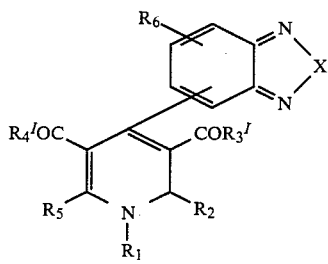

wherein $R_1$ is hydrogen, alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, phenylalkyl of 7 to 9 carbon atoms or phenylalkenyl of 9 to 12 carbon atoms, the phenyl ring being unsubstituted or mono-, di- or trisubstituted independently by halogen, hydroxy or alkyl or alkoxy of 1 to 4 carbon atoms, $R_2$ and $R_5$, independently are hydrogen or alkyl of 1 to 6 carbon atoms, $R_3{}^I$ and $R_4{}^I$, independently, are alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, alkoxy of 1 to 6 carbon atoms, hydroxyalkoxy of 2 to 6 carbon atoms, alkoxyalkoxy of 3 to 6 carbon atoms, hydroxyalkoxyalkoxy of 4 to 8 carbon atoms, alkenyloxy or alkinyloxy of 3 to 6 carbon atoms, cycloalkyloxy of 3 to 7 carbon atoms or cycloalkylalkoxy of 4 to 8 carbon atoms, $R_6$ is hydrogen, halogen, alkyl or alkoxy or alkylthio or alkylsulfonyl, each of 1 to 4 carbon atoms, trifluoromethyl, nitro or hydroxy, and X is oxygen or sulphur.

In any of the above radicals alkyl of 1 to 6 carbon atoms is preferably of 1 to 4 carbon atoms, especially of 1 or 2 carbon atoms. Any alkyl, alkoxy, alkylthio or alkylsulfonyl radical of 1 to 4 carbon atoms is preferably of 1 or 2 carbon atoms. The alkyl moiety of cycloalkylalkyl or cycloalkylalkoxy is conveniently methyl. Halogen means fluorine, chlorine or bromine and is especially chlorine. Cycloalkyl or the cycloalkyl moiety of cycloalkylalkyl or cycloalkylalkoxy is conveniently cyclopropyl or cyclopentyl or cyclohexyl. The multiple bond of alkenyl, alkinyl, alkenyloxy, alkinyloxy or phenylalkenyl is preferably not in the α, β position. Alkenyl, alkenyloxy, alkinyl or alkinyloxy preferably has 3 to 5 carbon atoms. Alkenyl or the alkenyl moiety of alkenyloxy is conveniently allyl or 2-methylallyl. Alkinyl or the alkinyl moiety of alkinyloxy is conveniently propinyl. Phenylalkenyl preferably has the trans-configuration and is for example cinnamyl. When $R_1$ is optionally substituted phenylalkyl, the phenyl group is preferably unsubstituted. When the phenyl group is di- or tri-substituted, preferably the substituents are the same. When $R_3{}^I$ and/or $R_4{}^I$ is alkoxy, this is preferably ethoxy or methoxy. When $R_3{}^I$ and/or $R_4{}^I$ is alkoxyalkoxy or hydroxyalkoxyalkoxy, preferably the carbon chain between the two ether oxygen atoms is of 2 carbon atoms. The hydroxy group of hydroxyalkoxy or of hydroxyalkoxyalkoxy is preferably not attached to the carbon atom attached to an ether oxygen atom. $R_1$ is preferably hydrogen. $R_2$ is conveniently identical to $R_5$. $R_2$ and/or $R_5$ is preferably methyl. $R_3{}^I$ and/or $R_4{}^I$ is preferably alkoxy or alkoxyalkoxy, especially n-butyloxyethoxy. $R_6$ is conveniently halogen, alkyl or alkoxy, or especially hydrogen. $R_6$ is conveniently adjacent to the dihydropyridine moiety which in turn is conveniently in the 4-position.

In the following examples all temperatures are in degrees Centigrade and are uncorrected.

EXAMPLE 1

4-(2,1,3-Benzoxadiazol-4-yl)-2,6-dimethyl-1,4-dihydropyridine-3,5-dicarboxylic acid diethyl ester 3.2 g of 2,1,3-benzoxadiazole-4-aldehyde, 5.7 g of acetoacetic acid ethyl ester, 2.5 ml of concentrated ammonia and 10 ml of ethanol are refluxed for 6 hours. The mixture is subsequently evaporated and the residual oil is chromatographed on silica gel with chloroform/acetic acid ethyl ester (9:1) to yield the title compound. The product is recrystallised from toluene, m.p. 153°–155°.

By using the process described in Example 1, and corresponding starting compounds, e.g. a compound of formula II, wherein —HC=Y is a radical i) and compounds of formula IV and V, and for Examples 18 and 19 a compound of formula II, wherein —HC=Y is a radical ii), wherein Z is oxygen and a compound of formula VI, the following compounds of formula Ia may be obtained, wherein y indicates the position of the dihydropyridine moiety:

| Example | $R_1$ | $R_2$ | $R_3{}^I$ | $R_4{}^I$ | $R_5$ | $R_6$ | X | y | m.p. |
|---|---|---|---|---|---|---|---|---|---|
| 2 | H | $CH_3$ | $OC_2H_5$ | $OC_2H_5$ | $CH_3$ | H | S | 4 | 146–148 |
| 3 | H | $CH_3$ | $OC(CH_3)_3$ | $OC(CH_3)_3$ | $CH_3$ | H | S | 4 | 193–199 |
| 4 | H | $CH_3$ | $OCH_3$ | $OCH_3$ | $CH_3$ | 7-Cl | O | 4 | 207–211 |
| 5 | H | $CH_3$ | $OCH_3$ | $OCH_3$ | $CH_3$ | H | S | 4 | 215–216 |
| 6 | H | $CH_3$ | $OC_2H_5$ | $OC_2H_5$ | $CH_3$ | 5-$OCH_3$ | S | 4 | 201–203 |
| 7 | H | $CH_3$ | $OC_2H_5$ | $OC_2H_5$ | $CH_3$ | 7-Cl | S | 4 | 135–155 |
| 8 | H | $CH_3$ | $OC_2H_5$ | $OC_2H_5$ | $CH_3$ | H | S | 5 | 152–153 |
| 9 | H | $CH_3$ | $OC_2H_5$ | $OC_2H_5$ | $CH_3$ | 4-Cl | S | 5 | 198–200 |
| 10 | H | $CH_3$ | $C(CH_3)_3$ | $C(CH_3)_3$ | $CH_3$ | H | S | 4 | |
| 11 | H | $CH_3$ | $CH_3$ | $CH_3$ | $CH_3$ | 7-Cl | O | 4 | |
| 12 | H | $CH_3$ | $CH_3$ | $CH_3$ | $CH_3$ | H | S | 4 | 225–228 |
| 13 | H | $CH_3$ | $C_2H_5$ | $C_2H_5$ | $CH_3$ | 5-$OCH_3$ | S | 4 | |
| 14 | H | $CH_3$ | $C_2H_5$ | $C_2H_5$ | $CH_3$ | 7-Cl | S | 4 | |
| 15 | H | $CH_3$ | $C_2H_5$ | $C_2H_5$ | $CH_3$ | H | S | 5 | |
| 16 | H | $CH_3$ | $C_2H_5$ | $C_2H_5$ | $CH_3$ | 4-Cl | S | 5 | |
| 17 | H | $CH_3$ | $CH_3$ | $CH_3$ | $CH_3$ | H | O | 4 | 218–222 |
| 18 | H | $CH_3$ | $CH_3$ | $OC_2H_5$ | $CH_3$ | H | O | 4 | 186–188 |

| Example | $R_1$ | $R_2$ | $R_3{}^I$ | $R_4{}^I$ | $R_5$ | $R_6$ | X | y | m.p. |
|---|---|---|---|---|---|---|---|---|---|
| 19 | H | $CH_3$ | $CH_3$ | $OC_2H_5$ | $CH_3$ | H | S | 4 | 146–148 |

EXAMPLE 20

4-(2,1,3-Benzoxadiazol-4-yl)-2,6-dimethyl-1,4-dihydro-3-methoxy carbonyl-pyridine-5-carboxylic acid isobutyl ester 3 g of 2,1,3-benzoxadiazole-4-aldehyde, 3.2 g of acetoacetic acid isobutyl ester, 2.3 g β-aminocrotonic acid methyl ester and 10 ml of ethanol are stirred under reflux for 3 hours. The mixture is subsequently evaporated and the residue is chromatographed on silica gel with chloroform/acetic acid ethyl ester (8:1) to yield the title compound. The product is recrystallised from diisopropyl ether and methylcyclohexane, m.p. 148°–158°.

By using the process described in Example 1, and corresponding starting compounds, e.g. a compound of formula II, wherein —HC═Y is a radical (i) and compounds of formula IV and V, and for Examples 23, 24 and 27 to 36 a compound of formula II, wherein —HC═Y is a radical (ii), wherein Z is oxygen and a compound of formula VI, the following compounds of formula Ia, wherein $R_2$ and $R_5$ are each methyl and $R_6$ is hydrogen, may be obtained, wherein y indicates the position of the dihydropyridine moiety:

| Comp. | $R_3{}^I$ | $R_4{}^I$ | $R_1$ | y | X | m.p. |
|---|---|---|---|---|---|---|
| 21 | $OCH_3$ | $OCH_3$ | H | 4 | O | 215–221 |
| 22 | $OC_2H_5$ | $OC_2H_5$ | H | 5 | O | 173–174 |
| 23 | $OCH_2CH(CH_3)_2$ | $OC_2H_5$ | H | 4 | S | 85–95 |
| 24 | $OCH_2CH(CH_3)_2$ | $OC_2H_5$ | H | 4 | O | 145–146.5 |
| 25 | $OC(CH_3)_3$ | $OC(CH_3)_3$ | H | 4 | O | 207–210 |
| 26 | $OCH_2CH(CH_3)_2$ | $OCH_2CH(CH_3)_2$ | H | 4 | O | 135.5-137 |
| 27 | $O(CH_2)_2OC_2H_5$ | $OC_2H_5$ | H | 4 | O | 126–128 |
| 28 | $O(CH_2)_2OC_2H_5$ | $OC_2H_5$ | H | 4 | S | oil |
| 29 | $O(CH_2)_2OC_2H_5$ | $OC_2H_5$ | H | 5 | S | 72–78 |
| 30 | $OCH(CH_3)_2$ | $OCH_3$ | H | 4 | O | 168–170 |
| 31 | $O(CH_2)_2OCH_3$ | $OCH_3$ | H | 4 | O | 151–153 |
| 32 | $O(CH_2)_2OCH(CH_3)_2$ | $OCH_3$ | H | 4 | O | 114–120 |
| 33 | $O(CH_2)_2OC_2H_5$ | $OCH_3$ | H | 4 | O | 140–147 |
| 34 |  | $OCH_3$ | H | 4 | O | 156–163 |
| 35 | $O(CH_2)_2OCH_3$ | $OCH(CH_3)_2$ | H | 4 | O | 119 |
| 36 | $OCH_3$ | $OC_2H_5$ | H | 4 | O | 159 |
| 37 | $OC_2H_5$ | $OC_2H_5$ | $CH_3$ | 4 | O | 106 |
| 38 | $OC_2H_5$ | $OC_2H_5$ | $n\text{-}C_3H_7$ | 4 | O | 99 |

In addition from a compound of formula II, wherein —HC═Y is a radical ii), wherein Z is oxygen and a compound of formula VI there may be made the following compounds of formula I, wherein y indicates the position of the dihydropyridine moiety:

| Ex. | $R_1$ | $R_2$ | $R_3$ | $R_4$ | $R_5$ | $R_6$ | X | y | m.p. |
|---|---|---|---|---|---|---|---|---|---|
| 39 | H | $CH_3$ | CN | COO—i-Bu | $CH_3$ | H | O | 4 | 123–124.5 |
| 40 | H | $CH_3$ | $COOC_2H_5$ | $SO_2CH_3$ | $CH_3$ | H | O | 4 | 204–205 |
| 41 | H | $CH_3$ | CN | $COOC_2H_5$ | $CH_3$ | H | O | 4 | 167–177 |
| 42 | H | $CH_3$ | CN | $COOC_2H_5$ | $CH_3$ | H | S | 4 | 187–190 |
| 43 | H | $CH_3$ | CN | $COOCH_2CH(CH_3)_2$ | $CH_3$ | H | S | 4 | 166–171 |
| 44 | H | $CH_3$ | $COOCH_3$ | $COC_6H_5$ | $CH_3$ | H | O | 4 | 192–201 |
| 45 | H | $CH_3$ | $COO(CH_2)_2N(CH_3)(CH_2C_6H_5)$ | $COOC_2H_5$ | $CH_3$ | H | O | 4 | 180–184** |
| 46 | H | $CH_3$ | $COO(CH_2)_2N(CH_3)(CH_2C_6H_5)$ | $COOC_2H_5$ | $CH_3$ | H | S | 4 | 173–175** |
| 47 | H | $CH_3$ | $COO(CH_2)_2N(CH_3)_2$ | $COO(CH_2)_2N(CH_3)_2$ | $CH_3$ | H | O | 4 | 188–191* fumarate |
| 48 | H | $CH_3$ | $COO(CH_2)_2N(CH_3)_2$ | $COO(CH_2)_2N(CH_3)_2$ | $CH_3$ | H | S | 4 | 156–159 fumarate |
| 49 | H | $CH_3$ | $COO(CH_2)_2N(CH_3)_2$ | $COOC_2H_5$ | $CH_3$ | H | O | 4 | |
| 50 | H | $CH_3$ | $COO(CH_2)_2N(CH_3)_2$ | $COOC_2H_5$ | $CH_3$ | H | S | 4 | 166–176 hydrogen-furmarate |

-continued

| Ex. | R$_1$ | R$_2$ | R$_3$ | R$_4$ | R$_5$ | R$_6$ | X | y | m.p. |
|---|---|---|---|---|---|---|---|---|---|
| 51 | H | CH$_3$ | COO(CH$_2$)$_2$N(CH$_3$)(CH$_2$C$_6$H$_5$) | COOC$_2$H$_5$ | CH$_3$ | H | S | 5 | oil |
| 52 | H | CH$_3$ | COO(CH$_2$)$_2$N(CH$_3$)(CH$_2$C$_6$H$_5$) | COOC$_2$H$_5$ | CH$_3$ | H | O | 5 | oil |
| 53 | H | CH$_3$ | COO(CH$_2$)$_2$N(CH$_3$)(CH$_2$C$_6$H$_5$) | COOCH$_3$ | CH$_3$ | H | O | 4 | 182–195** |
| 54 | H | △ | COOC$_2$H$_5$ | COOC$_2$H$_5$ | CH$_3$ | H | O | 4 | 97–99 |
| 55 | H | △ | COOCH$_3$ | COOCH$_3$ | CH$_3$ | H | O | 4 | 160–163 |
| 56 | H | △ | COOCH$_3$ | COOCH$_3$ | △ | H | O | 4 | 118–120 |
| 57 | H | △ | COOC$_2$H$_5$ | COOC$_2$H$_5$ | △ | H | O | 4 | 110–112 |
| 58 | H | CH$_3$ | COO(CH$_2$)$_2$—C$_6$H$_5$ | COOCH$_3$ | CH$_3$ | H | O | 4 | 156 |
| 59 | H | CH$_3$ | COOCH$_3$ | COOCH$_2$C$_6$H$_5$ | CH$_3$ | H | O | 4 | 131–136 |

*decomposition
**hydrochloride

| Ex. | R₁ | R₂ | R₃ | R₄ | R₅ | R₆ | y | X |
|---|---|---|---|---|---|---|---|---|
| a | CH₃ | H | CO—nC₆H₁₃ | CO—nC₆H₁₃ | H | 4-C₂H₅ | 5 | S |
| b | nC₆H₁₃ | n-C₆H₁₃ | CO—CH₂—CH=CHC₂H₅ | COCH₂CH=CHC₂H₅ | n-C₆H₁₃ | 6-SC₂H₅ | 5 | S |
| c | C₂H₅—CH=CH—CH₂ | H | cyclopropyl-CO— | cyclopropyl-CO— | H | 7-CH₃ | 5 | S |
| d | cyclopropyl | H | CH₃ (cyclopropyl-CO—) | cyclopropyl-CO— | H | 4-NO₂ | 5 | S |
| e | cyclohexyl | H | cyclohexyl-CO— | cyclohexyl-CO— | H | 4-OH | 5 | S |
| f | C₆H₅-CH₂ | H | COOCH₂OC₂H₅ | COOCH₂OC₂H₅ | H | H | 5 | S |
| g | 3-Cl-C₆H₄-(CH₂)₃ | H | COO(CH₂)₂OCH₂OH | COO(CH₂)₂OCH₂OH | H | H | 5 | S |
| h | 3-Cl-5-F-4-(CH₂)₃-C₆H₂ (C₂H₅O-) | H | COOCH₂CH=CH—C₂H₅ | COOCH₂—CH=CHC₂H₅ | H | H | 5 | S |
| i | 3-Cl-5-F-4-(CH₂)₃-C₆H₂ (Br-) | H | cyclopropyl-COO— | cyclopropyl-COO— | H | H | 5 | S |

-continued

| Ex. | R₁ | R₂ | R₃ | R₄ | R₅ | R₆ | y | X |
|---|---|---|---|---|---|---|---|---|
| j | 3-HO-C₆H₄-CH=CH-CH₂ | H | COO(CH₂)₄OH | COO(CH₂)₄OH | H | 7-SO₂C₂H₅ | 5 | S |
| k | C₂H₅-C≡C-CH₂ | H | | | H | | 5 | S |
| l | nC₆H₁₃ | nC₆H₁₃ | COCH₂-C≡CH | COCH₂-C≡CH | n-C₆H₁₃ | 7-CF₃ | 5 | S |
| m | cyclopropyl-CH₂ | H | COCH₂-cyclohexyl | COCH₂-cyclohexyl | H | 6-SC₂H₁₃ | 5 | S |
| n | 3-F,5-Br-2-(CH₂)₃-C₆H₂-Cl | H | COOCH₂-cyclopropyl | COOCH₂-cyclopropyl | H | 4-NO₂ | 5 | S |
| o | 3-Cl-C₆H₄-(CH₂)₃ | H | COOCH₂-C≡C-C₂H₅ | COOCH₂-C≡C-C₂H₅ | H | H | 5 | S |
| p | cyclopentyl-CH₂ | C₄H₉ | COOCH₂N(morpholino) | CO(CH₂)₃NHC₃H₇ | H | H | 5 | S |
| | | | | CH₂CH=CH₂ | | | | |
| q | CH₂C≡C-C₂H₅ | H | COO(CH₂)₃N< (CH₂)₂OH | COO(CH₂)₃N< (CH₂)₂OH | H | 7-OC₃H₇ | 5 | O |
| | | | | | H | 7-NHCOC₄H₉ | 5 | O |

-continued

| Ex. | $R_1$ | $R_2$ | $R_3$ | $R_4$ | $R_5$ | $R_6$ | y | X |
|---|---|---|---|---|---|---|---|---|
| r | (CH₂)₃–C₆H₅ | H | COO(CH₂)₂N[(CH₂)₂–C≡CH][CH₂-cyclopentyl] | S–iC₃H₇ | H | 6-nC₆H₁₃ | 5 | S |
| s | (CH₂)₃-cyclohexyl | H | COO(CH₂)₃N[(CH₂)₂NHC₃H₇][cyclopropyl] | SO₂C₄H₉ | H | 7-SO₂C₂H₅ | 5 | S |
| t | C₂H₅–C₆H₄(o-CH₂–CH=CH₃) | H | SO₂(CH₂)₃OC₂H₅ | SO₂(CH₂)₂C₆H₅ | H | 6-NO₂ | 5 | S |
| u | CH₃ | H | COCH₂C≡CH | COO(CH₂)₂CH(OH)CH₃ | H | 6-SO₂N(C₂H₅)(i-C₂H₅) | 5 | S |
| v | C₆H₅CH₂– | (CH₂)₃C₆H₅ | 3-pyridyl-CO– | COO(CH₂)₃OCH₃ | (CH₂)₂-cyclopentyl | 7-OCF₃ | 5 | S |
| w | CH₂–CH=CHC₂H₅ | cyclopentyl | S–CH₂-cyclobutyl | COO(CH₂)₄CH(CH₃)NH₂ | C₄H₉ | 6-N₃ | 4 | S |
| x | C₂H₅O–C₆H₂(F)(Cl)(CH₂)₂– | H | S–CH₂–C≡CH | COO(CH₂)₅–NHC₂H₅ | H | 7-F | | S |

-continued

| Ex. | $R_1$ | $R_2$ | $R_3$ | $R_4$ | $R_5$ | $R_6$ | y | X |
|---|---|---|---|---|---|---|---|---|
| y | $C_6H_5$ | H | cyclopentyl-SO- | triazole-COOCH | $C_3H_7$ | 7-COO—$NC_6H_{13}$ | 5 | S |
| z | 3-HO-C$_6$H$_4$-CH$_2$- | i-$C_3H_7$ | $SO_2CH_2OC_3H_7$ | $COO(CH_2)_3$-C(triazole)H | H | 6-OH | 4 | S |
| aa | 3-Cl-C$_6$H$_4$-(CH$_2$)$_3$- | H | $S(CH_2)_3O(CH_2)_2$—OH | thiophene-CO- | H | 6-$CF_3$ | 5 | S |
| ab | $nC_6H_{13}$ | $nC_6H_{13}$ | cyclobutyl-COO($CH_2)_3$ | cyclobutyl-CO- | $nC_6H_{13}$ | 7-NH—$iC_4H_9$ | 5 | S |
| ac | cyclopropyl-CH$_2$- | $(CH_2)_3C_6H_5$ | morpholinyl-$(CH_2)_2$-COO | morpholinyl-$(CH_2)_2$-COO | $(CH_2)_3C_6H_5$ | H | 5 | S |
| ad | 3,5-($OC_2H_5$)$_2$-C$_6$H$_3$- | H | $SO_2(CH_2)_3NHC_3H_7$ | $SO_2(CH_2)_3NHC_3H_7$ | H | 6-$SO_2N(C_3H_7)(C_2H_5)$ | 5 | O |
| ae | 2-$C_2H_5$-C$_6$H$_4$-CH$_2$- | H | pyrimidinyl-$SO_2(CH_2)_2$ | $SO_2(CH_2)_2$ | $C_3H_7$ | 7-$NO_2$ | 5 | S |

In addition from a compound of formula II, wherein —HC=Y is a radical ii), wherein Z is oxygen and a compound of formula VI there may be made the following compounds of formula Ia wherein X=S and the 1,4-dihydropyridine moiety is in the 5-position and $R_1$ to $R_6$ are respectively:

(a) $CH_3$; H; $nC_6H_{13}$; $nC_6H_{13}$; H; 4-$C_2H_5$; or (b) $nC_6H_{13}$; $nC_6H_{13}$; $C_2H_5.CH=CH.CH_2$; $C_2H_5.CH=CH.CH_2$; $nC_6H_{13}$; 6-$C_2H_5S$; or (c) $C_2H_5.CH=CH.CH_2$; H; ▷—; ▷—H; 7-$CF_3$; or (d) ▷—; H; cyclohexyl; cyclohexyl, H; 4-$NO_2$; or (e) cyclohexyl; H; $C_2H_5O.CH_2O$; $C_2H_5O.CH_2.O$; H; 4-OH; or (f) Ph-$CH_2$; H; $CH_2.O.C_2H_4.O$ with OH; $CH_2.O.C_2H_4O$ with OH; H; H; or (g) (3-Cl-phenyl)-$[CH_2]_3$; H; $C_2H_5.CH=CH.CH_2O$; $C_2H_5.CH=CH.CH_2O$; H; H; or (h) (2-$C_2H_5$-4-$C_2H_5O$-phenyl)-$[CH_2]_3$; H; cyclohexyl-O; cyclohexyl-O;

(i) (4-Br-2-F-5-Cl-phenyl)-$[CH_2]_3$; H; ▷—O; ▷—O; H; H;

(j) (3-OH-phenyl)-$CH=CH-CH_2$; H, $HO(CH_2)_4O-$;

$HO(CH_2)_4O-$; H; $C_2H_5SO_2$; or (k) $C_2H_5-C\equiv C-CH_2$; H; ▷—; ▷—H; 7-$CF_3$; or (l) $nC_6H_{13}$; $nC_6H_{13}$; $CH\equiv C-CH_2$; $CH\equiv C-CH_2$; $nC_6H_{13}$;

6-$C_2H_5S$; or (m) (3-Cl-phenyl)-$[CH_2]_3$; H; $C_2H_5-C\equiv C-CH_2O$;

$C_2H_5-C\equiv C-CH_2O$; H; H; or (n) ▷—$CH_2$; H; cyclohexyl-$CH_2$; cyclohexyl-$CH_2$; H; 4-$NO_2$; or (o) (4-Br-2-F-5-Cl-phenyl)-$[CH_2]_3$; H; ▷—$CH_2O$; ▷—$CH_2O$; H; H.

| | $R_1$ | $R_2$ | $R_3$ | $R_4$ | $R_5$ | $R_6$ | y | X |
|---|---|---|---|---|---|---|---|---|
| (p) | $C_4H_8C\equiv CH$ | $CH_3$ | CO—▢ | $COOCH_2C\equiv CH$ | $CH_3$ | 7-$OCF_3$ | 5 | S |
| (q) | $C\equiv C-C_2H_5$ | H | $COOCH_2$—▷ | $COOC_3H_6$—Ph | | $C_2H_5$ | 6-CN | 4 | S |
| (r) | Ph-CH(CH_3)— | | $CH_2$—▢ | $SOC_2H_4OC_2H_5$ | $COCH_2-CH=CH_2$ | $CH_2$—▢ | 7-$nC_4H_9$ | 4 | O |
| (s) | $C_4H_9$—▢ | $C_2H_5$ | CN | $CO(CH_2)_2N(C_3H_7)_2$ | $C_2H_5$ | 6-Br | 5 | S |
| (t) | $C_5H_{10}$—▷ | $C_2H_5$ | CN | $COOCH_2-C\equiv CH$ | $CH_3$ | 6-Br | 5 | S |

H; H; or

By using the process described in Example 1, and corresponding starting compounds, e.g. a compound of formula II, wherein —HC═Y is a radical (i) and compounds of formula IV and V, and for Examples 61, 62 and 65 to 74 a compound of formula II, wherein —HC═Y is a radical ii), wherein Z is oxygen and a compound of formula VI, the following compounds of formula I, wherein $R_2$ and $R_5$ are each methyl and $R_6$ is hydrogen, may be obtained, wherein y indicates the position of the dihydropyridine moiety and $R_3$ and $R_4$ are $COR_7{}^I$ and $COR_7{}^{II}$ respectively:

| Comp. | $R_7{}^I$ | $R_7{}^{II}$ | $R_1$ | y | X |
|---|---|---|---|---|---|
| 60 | $C_2H_5$ | $C_2H_5$ | H | 5 | O |
| 61 | $CH_2CH(CH_3)_2$ | $C_2H_5$ | H | 4 | S |
| 62 | $CH_2CH(CH_3)_2$ | $C_2H_5$ | H | 4 | O |
| 63 | $C(CH_3)_3$ | $C(CH_3)_3$ | H | 4 | O |
| 64 | $CH_2CH(CH_3)_2$ | $CH_2CH(CH_3)_2$ | H | 4 | O |
| 65 | $(CH_2)_2OC_2H_5$ | $C_2H_5$ | H | 4 | O |
| 66 | $(CH_2)_2OC_2H_5$ | $C_2H_5$ | H | 4 | S |
| 67 | $(CH_2)_2OC_2H_5$ | $C_2H_5$ | H | 5 | S |
| 68 | $CH(CH_3)_2$ | $CH_3$ | H | 4 | O |
| 69 | $(CH_2)_2OCH_3$ | $CH_3$ | H | 4 | O |
| 70 | $(CH_2)_2OCH(CH_3)_2$ | $CH_3$ | H | 4 | O |
| 71 | $(CH_2)_2OC_2H_5$ | $CH_3$ | H | 4 | O |
| 72 |  | $CH_3$ | H | 4 | O |
| 73 | $(CH_2)_2OCH_3$ | $CH(CH_3)_2$ | H | 4 | O |
| 74 | $CH_3$ | $C_2H_5$ | H | 4 | O |
| 75 | $C_2H_5$ | $C_2H_5$ | $CH_3$ | 4 | O |
| 76 | $C_2H_5$ | $C_2H_5$ | n-$C_3H_7$ | 4 | O |

The compounds of formula I exhibit pharmacological activity. In particular, they lead to a dilation of the coronary vessels as demonstrated by the results of tests measuring the blood flow to the myocardium of an anaesthetised cat by means of the microsphere method (Rudolph A. M. and Heymann M. S.: *Circulation Research* 21, 163, 1967) upon administration of from 30 to 50 μg/kg i.v. or of from 50 to 150 μg/kg i.d. of the active substance.

The compounds of formula I also possess a favourable effect against angina pectoris, as shown by the increase of the coronary flow of an anesthetised cat upon administration of the active substance.

The compounds of formula I are useful in the treatment of coronary insufficiency. For the above-mentioned use the dosage will, of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

The compounds of formula I increase the blood flow to limbs, e.g. leg musculature, as can be shown by means of the microsphere method on the anaesthetised cat upon administration of from 30 to 50 μg/kg i.v. or from 50 to 150 μg/kg i.d. of the compounds.

The compounds of formula I are therefore useful for treatment of intermittent claudication and other peripheral disturbances of blood flow to limb muscles. For the above-mentioned use the dosage will, of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

The compounds of formula I increase cerebral blood flow, as can be shown by means of the microsphere method on the anesthetised cat upon administration of from 30 to 50 μg/kg i.v. or from 50 to 150 μg/kg i.d. of the compounds.

The compounds of formula I are therefore useful in the treatment of cerebrovascular insults (accidents). For the above-mentioned use the dosage will, of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

The compounds of formula I possess calciumantagonistic activity, as indicated in standard tests, for example by an inhibition of a calcium induced contraction of isolated dog coronary arteries suspended in a depolarizing solution at concentration of $10^{-10}$ to $10^{-8}$M of the compounds according to the principles of Godfraind and Kaba, *Brit. J. Pharm.* 36, 549–560, 1969. The compounds are therefore useful as spasmolytic agents, for the treatment of spasms in muscles. For the above-mentioned use the dosage will of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

Additionally, the compounds of formula I exhibit antihypertensive activity, as indicated by a blood pressure lowering activity in standard tests.

For example, the compounds exhibit a blood pressure lowering effect in the Grollman rat test [see A. Grollman, *Proc. Soc. Expt. Biol. and Med.* 57, 104 (1944)] on s.c. administration of from 0.1 to 10 mg/kg animal body weight of the compounds.

The compounds are therefore useful as anti-hypertensive agents. For this use the dosage will, of course, vary depending on the compound employed, mode of administration and therapy desired. However, in general, satisfactory results are obtained with a daily dosage of from 0.5 to 50 mg/kg animal body weight, conveniently given in divided doses 2 to 4 times a day or in sustained release form. For the larger mammal, the total daily dosage is in the range form about 5 to about 1000 mg, e.g. 30 to 1000 mg, and dosage forms suitable for oral administration comprise from about 1.25 mg to about 500 mg of the compounds admixed with a solid or liquid pharmaceutical carrier or diluent.

A compound of formula I may be administered in free base form. Alternatively any sufficiently basic compound of formula I, e.g. those compounds wherein $R_3$ or $R_4$ contain an amino moiety, may be administered in pharmaceutically acceptable acid addition salt form. Such acid addition salt forms exhibit the same order of activity as the free base forms. The present invention also provides a pharmaceutical composition comprising a compound of formula I in association with a pharmaceutical carrier or diluent. Such compositions may be prepared by conventional techniques to be in conventional forms, for example capsules or tablets.

The compounds of Examples 1, 20, 24, 30-38, 45, 53 and 59 are particularly interesting. The coronary insufficiency, the intermittent claudication, the cerebrovascular insufficiency and the spasmolytic activities are the preferred utilities for compounds of formula I.

In a group of compounds of formula Ia $R_1$ is hydrogen, alkyl, alkenyl, cycloalkyl of 3 to 6 carbon atoms, phenylalkyl, or phenylalkenyl; the phenyl ring being unsubstituted or substituted by one, two or three substituents chosen form one or two halogen radicals, one or two alkyl groups of 1 to 4 carbon atoms, one to three alkoxy groups of 1 to 4 carbon atoms; $R_3{}^I$ and $R_4{}^I$, independently, are alkyl, alkenyl, cycloalkyl of 3 to 6 carbon atoms, alkoxy, hydroxyalkoxy of 2 to 6 carbon atoms, alkoxyalkoxy of 3 to 6 carbon atoms, hydroxyalkoxyalkoxy of 4 to 8 carbon atoms, alkenyloxy, or cycloalkyloxy of 3 to 6 carbon atoms, and $R_6$ is other than alkylsulfonyl.

Conveniently $R_1$ is hydrogen, $R_2$ and $R_5$ are each alkyl, especially methyl, $R_3{}^I$ and $R_4{}^I$ are each alkoxy, especially ethoxy, $R_6$ is hydrogen or halogen, especially chlorine, especially in the 4 position, the dihydropyridine moiety is in the 4 or 5 position, and X is S.

Alternatively conveniently $R_1$ is hydrogen, $R_2$ and $R_5$ are each alkyl, especially methyl, $R_3{}^I$ and $R_4{}^I$ are alkyl or alkoxy, especially methyl, ethyl, tert. butyl, methoxy, ethoxy or tert.butyloxy, $R_6$ is hydrogen or halogen, especially chlorine, or alkoxy, especially methoxy, the dihydropyridine moiety is in the 4 or 5 position and $R_6$ is in the 4, 5 or 7 position.

In one group of compounds of formula I
$R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$),
$R_2$ and $R_5$, independently, are hydrogen, alkyl($C_{1-6}$) or phenylalkyl($C_{7-10}$),
$R_3$ and $R_4$, independently are CN, $COR_7$, $COOR_7$ or $S(O)_nR_7$,
wherein
n is 0, 1 or 2,
$R_7$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl ($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), phenyl, phenylalkyl($C_{7-10}$), a 5- or 6-membered heterocyclic ring containing one heteroatom selected from nitrogen, oxygen or sulphur, or alkyl ($C_{1-4}$) substituted by a 5- or 6-membered heterocyclic ring containing one heteroatom selected from nitrogen, oxygen or sulphur, $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro, hydroxy, azido, amino, alkyl($C_{1-4}$)amino, alkanoyl($C_{1-5}$)amino, carbalkoxy($C_{2-4}$), aminocarbonyl, trifluoromethoxy, cyano, sulfamyl, alkyl($C_{1-4}$)sulfamyl or di[alkyl($C_{1-4}$)]sulfamyl, and
X is oxygen or sulphur, with the proviso that when $R_1$ is hydrogen, alkyl($C_{1-6}$), alkenyl($C_{3-6}$), alkinyl ($C_{3-6}$), cycloalkyl($C_{3-7}$), cycloalkylalkyl($C_{4-8}$), phenylalkyl($C_{7-9}$) or phenylalkenyl($C_{9-12}$), the phenylring being unsubstituted or mono-, di- or trisubstituted independently by halogen, hydroxy, alkyl($C_{1-4}$) or alkoxy($C_{1-4}$),
$R_2$ and $R_5$, independently, are hydrogen or alkyl($C_{1-4}$),
$R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro or hydroxy, and
X is oxygen or sulphur, then at least one of the substituents $R_3$ and $R_4$ is other than $COR_7{}^I$, wherein $R_7{}^I$ is alkyl($C_{1-6}$), alkenyl($C_{3-6}$), alkinyl($C_{3-6}$), cycloalkyl($C_{3-7}$), cycloalkylalkyl($C_{4-8}$), and is other than $COOR_7{}^{II}$, wherein $R_7{}^{II}$ is alkyl($C_{1-6}$), alkenyl ($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$) or hydroxyalkoxyalkyl($C_{4-8}$).

In another group of compounds of formula I
$R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$),
$R_2$ and $R_5$, independently, are hydrogen, alkyl($C_{1-6}$) or phenylalkyl($C_{7-10}$),
$R_3$ is

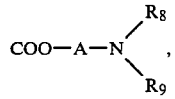

and
$R_4$ is CN, $COR_7$, $COOR_7$, $S(O)_nR_7$ or

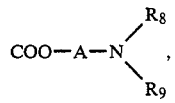

wherein
n is 2,
$R_7$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), phenyl or phenylalkyl($C_{7-10}$),
A is alkylene($C_{1-6}$),
$R_8$ and $R_9$, independently, are alkyl($C_{1-6}$), alkenyl or alkinyl($C_{3-6}$), cycloalkyl($C_{3-7}$), cycloalkylalkyl ($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), phenyl, phenylalkyl($C_{7-10}$), or
$R_8$ and $R_9$ together with the nitrogen atom form a 5-, 6- or 7-membered heterocyclic ring, which may contain a further heteromember selected from oxygen, sulphur and a group =N—$R_{10}$, wherein $R_{10}$ is alkyl ($C_{1-4}$), and $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro, hydroxy, azido, amino, alkyl($C_{1-4}$)amino, alkanoyl($C_{1-5}$)amino, carbalkoxy($C_{2-5}$), aminocarbonyl, trifluoromethoxy, cyano or sulfamyl, and X is oxygen or sulphur.

In another group of compounds of formula I $R_1$ is hydrogen, alkyl($C_{1-6}$), alkenyl($C_{3-6}$), alkinyl ($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently, are $COR_7^I$ or $COOR_7^{II}$, wherein $R_7^I$ is alkyl($C_{1-6}$), alkenyl($C_{3-6}$), alkinyl($C_{3-6}$), cycloalkyl($C_{3-7}$), cycloalkylalkyl($C_{4-8}$), and $R_7^{II}$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$) or hydroxyalkoxyalkyl ($C_{4-8}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro or hydroxy, and X is oxygen or sulphur, with the proviso, that at least one of the substituents $R_2$ and $R_5$ is phenylalkyl ($C_{7-10}$), cycloalkyl($C_{3-7}$) or cycloalkylalkyl($C_{4-8}$).

A group of compounds are compounds of formula I, wherein $R_1$ is alkyl($C_{1-6}$), alkoxyalkyl($C_{3-6}$), alkenyl($C_{3-6}$), alkinyl($C_{3-6}$), cycloalkyl($C_{3-7}$), $R_2$ and $R_5$, independently, are hydrogen or alkyl($C_{1-6}$), $R_3$ and $R_4$, independently, are $COOR_7$, wherein $R_7$ is other than phenylalkyl.

These compounds show surprisingly beneficial pharmacological activity than is expected for compounds of this type, e.g. long lasting coronary sufficiency activity in the tests mentioned above and good tolerability.

In another group of formula I $R_1$ is alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl ($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently are CN, $COR_7$, $COOR_7$, $S(O)_nR_7$ or

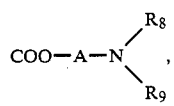

subject to the proviso as defined above, provided that $R_3$ and $R_4$ are not both $COOR_7$, wherein $R_7$ is alkyl($C_{1-6}$).

In another group of compounds of formula I $R_1$ is alkyl($C_{1-6}$), alkenyl($C_{3-6}$), alkinyl($C_{3-6}$), cycloalkyl($C_{3-7}$), $R_2$ and $R_5$, independently, are hydrogen or alkyl($C_{1-6}$), $R_3$ and $R_4$, independently, are CN, $COR_7$, $COOR_7$, $S(O)_nR_7$ or

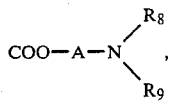

wherein n, $R_7$, A, $R_8$ and $R_9$ and subject to the proviso as defined above and provided that $R_3$ and $R_4$ are not both $COOR_7$, wherein $R_7$ is alkyl($C_{1-6}$).

In a sub-group $R_6$ is alkylsulfonyl($C_{1-4}$), hydroxy, azido, amino, alkyl($C_{1-4}$)amino, di[alkyl($C_{1-4}$)]amino, alkanoyl($C_{1-5}$)amino, aminocarbonyl, tri-fluoromethoxy, sulfamyl, alkyl($C_{1-4}$)sulfamyl or di[alkyl($C_{1-4}$)]sulfamyl.

In another group of compounds of formula I $R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl ($C_{8-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently are CN, $COR_7$, $COOR_7$, $S(O)_nR_7$ or

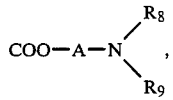

wherein n, $R_7$, A, $R_8$ and $R_9$ and subject to the proviso as defined above, provided that $R_3$ and $R_4$ are not independently $COR_7$, wherein $R_7$ is alkyl($C_{1-6}$), alkenyl($C_{3-6}$), alkinyl($C_{3-6}$) or $COOR_7$, wherein $R_7$ is other than phenyl or phenylalkyl as defined above.

In a first group of compounds $R_1$ is hydrogen.

In a second group of compounds $R_1$ is alkyl.

In a third group of compounds $R_1$ is hydroxyalkyl.

In a fourth group of compounds $R_1$ is alkoxyalkyl.

In a fifth group of compounds $R_1$ is alkenyl.

In a sixth group of compounds $R_1$ is alkinyl.

In a seventh group of compounds $R_1$ is cycloalkyl.

In an eighth group of compounds $R_1$ is cycloalkylalkyl.

In a ninth group of compounds $R_1$ is phenylalkyl.

In a tenth group of compounds $R_1$ is phenylalkenyl.

In an eleventh group of compounds $R_2$ is alkyl.

In a twelfth group of compounds $R_2$ is hydrogen.

In a thirteenth group of compounds $R_2$ is phenylalkyl.

In a fourteenth group of compounds $R_2$ is cycloalkyl.

In a fifteenth group of compounds $R_2$ is cycloalkylalkyl.

In a sixteenth group of compounds $R_5$ is alkyl.

In a seventeenth group of compounds $R_5$ is hydrogen.

In an eighteenth group of compounds $R_5$ is phenylalkyl.

In a nineteenth group of compounds $R_5$ is cycloalkyl.

In a twentieth group of compounds $R_5$ is cycloalkylalkyl.

In a twentyfirst group of compounds $R_5$ is identical to $R_5$.

In a twentysecond group of compounds $R_5$ is a different radical type from $R_2$.

In a twentythird group of compounds R₃ is identical to R₄.

In a twentyfourth group of compounds R₃ is a different radical type from R₄.

In a twentyfifth group of compounds $R_3{}^I$ is a different radical type from $R_4{}^I$.

In a twentysixth group of compounds R₃ independently is COR₇.

In a twentyseventh group of compounds R₃ independently is COOR₇.

In a twentyeighth group of compounds R₃ independently is SR₇.

In a twentyninth group of compounds R₃ independently is SOR₇.

In a thirtieth group of compounds R₃ independently is SO₂R₇.

In a thirtyfirst group of compounds R₃ independently is

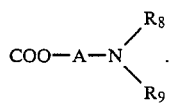

In a thirtysecond group of compounds R₄ is COR₇.
In a thirtythird group of compounds R₄ is COOR₇.
In a thirtyfourth group of compounds R₄ is SR₇.
In a thirtyfifth group of compounds R₄ is SOR₇.
In a thirtysixth group of compounds R₄ is SO₂R₇.
In a thirtyseventh group of compounds R₄ is COO—A—NR₈R₄.

In a thirtyeighth group of compounds R₇ is alkyl.
In a thirtyninth group of compounds R₇ is alkenyl.
In a fourtieth group of compounds R₇ is alkinyl.
In a fourtyfirst group of compounds R₇ is cycloalkyl.
In a fourtysecond group of compounds R₇ is cycloalkyl.
In a fourtythird group of compounds R₇ is cycloalkylalkyl.
In a fourtyfourth group of compounds R₇ is hydroxyalkyl.
In a fourtyfifth group of compounds R₇ is alkoxyalkyl.
In a fourtysixth group of compounds R₇ is hydroxyalkoxyalkyl.
In a fourtyseventh group of compounds R₇ is aminoalkyl.
In a fourtyeighth group of compounds R₇ is alkylaminoalkyl.
In a fourtyninth group of compounds R₇ is di[alkyl]aminoalkyl.
In a fiftieth group of compounds R₇ is phenyl.
In a fiftyfirst group of compounds R₇ is phenylalkyl.

In a fiftysecond group of compounds R₇ is a heterocyclic ring.

In a fiftythird group of compounds R₇ is an alkyl group substituted by a heterocyclic ring.

In a fiftyfourth group of compounds A is ethylene.
In a fiftyfifth group of compounds X is oxygen.
In a fiftysixth group of compounds X is sulphur.

Any of the above groups may be combined to produce e.g. groups wherein the dihydropyridine substituents in positions 3 and 5, and/or 2 and 6 are identical, different or of a different type (e.g. are grouped in separate groups above).

What we claim is:

1. A compound having the formula

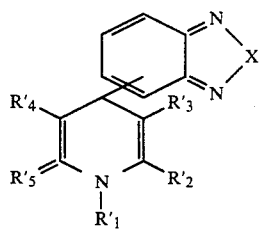

wherein
R₁' is hydrogen or C₁₋₆ alkyl;
R₂' and R₅', independently, are hydrogen or C₁₋₆ alkyl;
R₃' and R₄', independently, are COOR₇' or

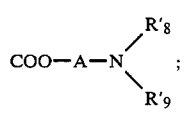

each R₇', independently, is C₁₋₆ alkyl, C₃₋₇ cycloalkyl, C₇₋₁₀ phenylalkyl, C₃₋₆ alkoxyalkyl, C₂₋₆-hydroxyalkyl or C₄₋₈ hydroxyalkoxyalkyl;
A is C₁₋₆ alkylene;
each R₈' and R₉', independently, is C₁₋₆ alkyl or C₇₋₁₀ phenylalkyl; and
X is oxygen or sulphur, with the proviso that at least one of R₃' and R₄' is COOR₇'
where R₇' is C₂₋₆ hydroxyalkyl or C₄₋₈ hydroxyalkoxyalkyl, or a pharmaceutically acceptable acid addition salt of a basic compound of the above formula.

2. A compound of claim 1 wherein R₇' is C₂₋₆ hydroxyalkyl.

3. A compound of claim 1 wherein R₇' is C₄₋₈ hydroxyalkoxyalkyl.

4. A compound of claim 1 wherein R₁' is hydrogen.

* * * * *